United States Patent
France et al.

(10) Patent No.: US 11,207,322 B2
(45) Date of Patent: Dec. 28, 2021

(54) METHOD AND COMPOSITION RELATED TO COMBINATION THERAPY FOR ADDICTION

(71) Applicants: Charles France, San Antonio, TX (US); Gregory Collins, San Antonio, TX (US)

(72) Inventors: Charles France, San Antonio, TX (US); Gregory Collins, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 2 days.

(21) Appl. No.: 16/608,631

(22) PCT Filed: Apr. 27, 2018

(86) PCT No.: PCT/US2018/029802
§ 371 (c)(1),
(2) Date: Oct. 25, 2019

(87) PCT Pub. No.: WO2018/200959
PCT Pub. Date: Nov. 1, 2018

(65) Prior Publication Data
US 2020/0188396 A1 Jun. 18, 2020

Related U.S. Application Data

(60) Provisional application No. 62/491,920, filed on Apr. 28, 2017.

(51) Int. Cl.
*A61K 31/506* (2006.01)
*A61P 25/30* (2006.01)
*A61K 31/55* (2006.01)

(52) U.S. Cl.
CPC ............ *A61K 31/506* (2013.01); *A61K 31/55* (2013.01); *A61P 25/30* (2018.01)

(58) Field of Classification Search
CPC ........ A61K 31/506; A61K 31/55; A61P 25/30
See application file for complete search history.

(56) References Cited

U.S. PATENT DOCUMENTS

| 5,185,329 A | 2/1993 | Gawin et al. |
| 2004/0180875 A1 | 9/2004 | Lee et al. |
| 2014/0073664 A1 | 3/2014 | Wang et al. |
| 2015/0374712 A1 | 12/2015 | Green et al. |

FOREIGN PATENT DOCUMENTS

| WO | WO 2015/066344 | 5/2015 |
| WO | WO2015/066344 A1 * | 5/2015 |

OTHER PUBLICATIONS

International Search Report and Written Opinion issued in counterpart International Patent Application No. PCT/US2018/029802, dated Jul. 20, 2018.

* cited by examiner

*Primary Examiner* — Timothy R Rozof

(57) ABSTRACT

Certain embodiments are directed to methods of treating or preventing an addictive behavior in a subject by administering to the subject an effective amount of a 5-HT$_{2C}$ receptor agonist in combination with a DA D3/D4 receptor antagonist.

14 Claims, 6 Drawing Sheets

METHOD AND COMPOSITION RELATED TO COMBINATION THERAPY FOR ADDICTION

CROSS REFERENCE TO RELATED APPLICATION

This application is a national phase under 35 U.S.C. § 371 of International Application No. PCT/US2018/029802, filed Apr. 27, 2018, which claims the benefit of priority of U.S. Provisional Patent Application No. 62/491,920, filed Apr. 28, 2017, the entire contents of each of which are hereby incorporated by reference in their entirety.

BACKGROUND OF THE INVENTION

A. Field of the Invention

The invention generally concerns compositions and methods for the treatment of addiction. In particular the compositions and methods include the combination of a post-synaptic regulator of dopamine (DA) neurotransmission—antagonist or partial agonist at DA D3/D4 receptors (e.g., buspirone (Buspar®)) and a pre-synaptic regulator of DA neurotransmission—agonist at the serotonin $(5-HT)_{2C}$ receptor (e.g., lorcaserin (Belviq®)).

B. Description of the Related Art

The recreational use and/or abuse of drugs remains a significant public health problem, with worldwide estimates suggesting that 1 out of every 20 adults, or a quarter of a billion people, used at least one drug of abuse (e.g., cocaine) in 2014. Although the use of cocaine by Americans peaked in the 1980s, it has remained relatively stable over the past 30 years, with recent estimates suggesting that 1.9 million Americans regularly use cocaine; worldwide, there are an estimated 19 million regular users of cocaine. Despite long-standing efforts to develop pharmacotherapies, the U.S. Food and Drug Administration (FDA) has yet to approve a single medication for treating cocaine abuse.

Cocaine inhibits monoamine uptake at DA (DAT), serotonin (SERT), and norepinephrine (NET) transporters; however, its abuse-related effects are mediated predominantly by its capacity to increase DA neurotransmission. Indeed, it is well established that increases in synaptic levels of DA, particularly within the nucleus accumbens (NAcc), play a critical role in the abuse-related effects of not only cocaine, but also a wide variety of drugs that do not interact directly with DAT, such as opioids, ethanol, barbiturates, and nicotine. Because of this central role, drugs targeting DA systems have received considerable attention as candidate medications for cocaine abuse (i.e., drugs that decrease cocaine use and/or prolong periods of abstinence from cocaine). Accordingly, three basic strategies have been employed for developing pharmacotherapies for cocaine abuse: (1) direct or indirect DA receptor agonists, which aim to provide a replacement drug for cocaine; (2) cocaine antagonists, which aim to block cocaine at its site(s) of action; and (3) modulators of cocaine, which aim to alter the effects of cocaine through actions at sites other than DAT or DA receptors. Although such rational approaches to drug development have the potential to be truly transformative, they come with a substantial and ever growing price tag. Recent estimates from the Tufts Center for the Study of Drug Development suggest that a new drug requires ~10 years and $2.8 billion in R&D investments to obtain FDA approval.

There remains a need for additional therapies and regimens to treat various forms of addiction.

SUMMARY

One strategy to reduce the time and cost associated with developing pharmacotherapies for addiction has been to rationally repurpose drugs already FDA-approved for other indications. By selecting drugs based on their capacity to engage biologic targets already known to be important (i.e., neural substrates of addiction), such an approach dramatically reduces the time and costs associated with getting a candidate medication in the clinic. Aspects of the present invention are directed to compositions and methods that include two FDA-approved drugs, buspirone (Buspar®), an antagonist at DA D3/D4 receptors, and lorcaserin (Belviq®) an agonist at the $(5-HT)_{2C}$ receptor that indirectly modulates DA neurotransmission. These drugs have complementary mechanisms of action, and because they differentially target pre-synaptic (lorcaserin) and post-synaptic (buspirone) regulators of DA neurotransmission, the inventors contemplated that combinations of buspirone and lorcaserin, or drugs with similar pharmacology, will produce a therapeutic effect. Surprisingly, the combination of a DA D3/D4 receptor antagonist (buspirone) and a $(5-HT)_{2C}$ receptor agonist (lorcaserin) produced a therapeutic effect that is greater than the effect of either drug alone (i.e., a supra-additive interaction). Data from 4 rhesus monkeys support this effect, and indicate that combining these two classes of drugs can provide a novel, effective, and highly translatable pharmacotherapy for treating drug addiction/abuse, such as cocaine abuse.

As used herein the term "antagonist" refers to a compound that is capable of (i) altering the conformational state of a receptor by destabilizing the active conformation of that receptor and/or maintaining the receptor in its inactive conformation to thereby prevent it from binding its natural ligand; and/or (ii) binding to the receptor and preventing, decreasing or attenuating activation of that receptor. In certain aspects partial agonist can function as an antagonist by activating the receptor at a low but insufficient level, thus effectively antagonizing the receptor and its down steam signaling pathways.

As used herein the term "agonist" refers to a compound that is capable of (i) altering the conformational state of a receptor by stabilizing the active conformation of that receptor and/or maintaining the receptor in its active conformation; and/or (ii) binding to the receptor activating or increasing the activity of that receptor.

Recent studies indicate that lorcaserin (Belviq®) or buspirone (Buspar®) administered as a solo therapy can reduce cocaine self-administration in rhesus monkeys; however, these effects have been modest. Because these two drugs have potentially complementary mechanisms of action, the inventors conducted a study to evaluate the effectiveness of combinations of lorcaserin and buspirone, mixed at fixed ratios of 3:1, 1:1, and 1:3 (relative to each drugs $ED_{50}$), to reduce responding for 0.032 mg/kg/inf cocaine under a progressive ratio schedule in four rhesus monkeys (2 male and 2 female; see FIG. 1 for example). Dose addition analyses were used to determine if the effects of the drug combinations differed from those predicted for an additive interaction between lorcaserin and buspirone. When administered alone, lorcaserin and buspirone both inhibited responding in a dose-dependent manner. A similar dose dependent inhibition of cocaine self-administration was observed with each of the fixed dose combinations of lorcaserin and buspirone; however, all three of the lorcaserin:buspirone combinations were more potent than predicted for an additive interaction suggesting that lorcaserin and buspirone exhibit a supra-additive interaction with regard to their capacity to inhibit the reinforcing effects of cocaine. Together, these results indicate that a combination therapy containing a mixture of a DA D3/D4 receptor antagonist (e.g., buspirone) and a (5-HT)$_{2C}$ receptor agonist (e.g., lorcaserin) can be more effective than either monotherapy at reducing cocaine abuse.

A "combination therapy" refers to a therapy wherein both a DA D3/D4 receptor antagonist and a (5-HT)$_{2C}$ receptor agonist are to a subject. The DA D3/D4 receptor antagonist and the (5-HT)$_{2C}$ receptor agonist may be co-administered or co-formulated for administration. They may be administered separately or at different times. A preferred DA D3/D4 receptor antagonist is buspirone. A preferred (5-HT)$_{2C}$ receptor agonist is lorcaserin. The combination therapy may be administered for the purpose of treating an addiction.

Antagonist of DA D3/D4 receptors can include, but is not limited to buspirone, PG 01037, SB 277011A, trifluoperazine, A-381393, L-745,870, L-750,667, L-741,742, S18126, fananserin, clozapine, FAUC 213, sonepiprazole, PD 168568 dihydrochloride, PNU 96415E or salts thereof.

Agonist of (5-HT)$_{2C}$ receptor can include, but is not limited to lorcaserin, CP 809101, Ro-60-0175, WAY 161503, WAY 163909, MK 212, meta-chlorophenylpiperazine (mCPP), 1-methylpsilocin, Org 12962 hydrochloride, or salts thereof.

"Treating", includes any effect, e.g., lessening, reducing, modulating, or eliminating, that results in the improvement of the condition, disease, disorder, etc.

Preferably, the term "Subject" refers to a mammal. More preferably, the term subject refers to a primate. More preferably, the term subject refers to a human.

"Pharmaceutically or Pharmacologically Acceptable" include molecular entities and compositions that do not produce an adverse, allergic or other untoward reaction when administered to an animal, or a human, as appropriate.

"Pharmaceutically Acceptable Carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "therapeutically effective amount" as used herein refers to the amount of an agent, compound, drug, composition, or drug combination of the invention that is effective for producing some desired therapeutic effect upon administration to a subject or patient (e.g., a human subject or patient).

The phrase administering to a subject or administering to a patient refers to the process of introducing an agent, compound, drug, composition or drug combination of the invention into the subject or patient's body via an art-recognized means of introduction (e.g., orally, transdermally, via injection, etc.).

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
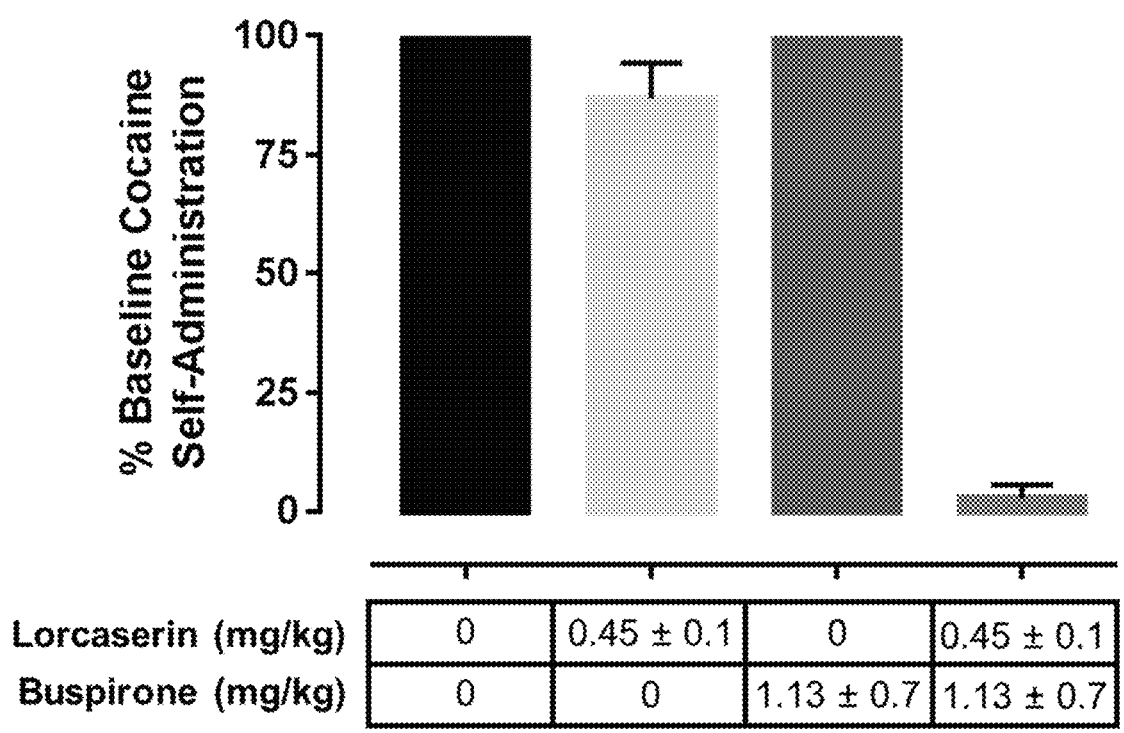
FIG. 1. Effects of 1:1 mixture of lorcaserin:buspirone on cocaine self-administration in rhesus monkeys.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be an example of that embodiment, and not intended to indicate that the scope of the disclosure, including the claims, is limited to that embodiment.

Lorcaserin, currently marketed under the trade name Belviq™ and previously Lorqess during development, is a weight-loss drug developed by Arena Pharmaceuticals. It has serotonergic properties and acts as an anorectic. Lorcaserin is a selective $(5\text{-}HT)_{2C}$ receptor agonist, and in vitro testing of the drug showed reasonable selectivity for $(5\text{-}HT)_{2C}$ over other related targets. $(5\text{-}HT)_{2C}$ receptors are located almost exclusively in the brain, and can be found in the choroid plexus, cortex, hippocampus, cerebellum, amygdala, thalamus, and hypothalamus. The activation of $(5\text{-}HT)_{2C}$ receptors in the hypothalamus is supposed to activate proopiomelanocortin (POMC) production and consequently promote weight loss through satiety. While it is generally thought that $(5\text{-}HT)_{2C}$ receptors help to regulate appetite as well as mood, and endocrine secretion, the exact mechanism of appetite regulation is not yet known. Lorcaserin has shown 100× selectivity for $(5\text{-}HT)_{2C}$ versus the closely related 5-HT2B receptor, and 17× selectivity over the 5-HT2A receptor.

Buspirone, brand name Buspar™, is an anxiolytic drug that is primarily used to treat generalized anxiety disorder (GAD). It is also commonly used to augment antidepressants in the treatment of depression. Unlike most anxiolytics, the pharmacology of buspirone is not related to that of benzodiazepines, barbiturates, or carbamates (it is not a GABA receptor agonist), and so buspirone does not carry the risk of physical dependence and withdrawal symptoms for which those drug classes are known. Buspirone is not considered a drug-of-abuse, is safer in overdose than traditional anxiolytics, and is significantly less impairing at therapeutic doses.

I. Dosages, Administration and Pharmaceutical Compositions

The choice of appropriate dosages for the drugs used in a combination therapy according to the present invention can be determined and optimized by the skilled artisan, e.g., by observation of the patient, including the patient's overall health, the response to the combination therapy, and the like. Optimization, for example, may be necessary if it is determined that a patient is not exhibiting the desired therapeutic effect or conversely, if the patient is experiencing undesirable or adverse side effects that are too many in number or are of a troublesome severity.

Preferably, one or more of the components of the combination therapy of the invention is/are prescribed at or below a dosage routinely used by the skilled artisan (e.g., physician) to promote the desired therapeutic effect of the drug, when the drug is used as a monotherapy.

In one embodiment, components of the combination (e.g., DA D3/D4 receptor antagonist and/or a $(5\text{-}HT)_{2C}$ receptor agonist) is/are prescribed at a dose that is below the typically described dose for each component as a monotherapy. The components may be prescribed separately or as a combination dosage.

In one embodiment, each component of the combination (e.g., DA D3/D4 receptor antagonist and a serotonin (5-HT)$_{2C}$ receptor agonist) is prescribed at a dose that is above the typically described dose for each component as a monotherapy. The components may be prescribed separately or as a combination dosage.

In another embodiment, the prescribed dosage of the DA D3/D4 receptor antagonist is above the typically described dose for monotherapy, and the $(5\text{-}HT)_{2C}$ receptor agonist is prescribed at a dosage that is at or below the typically described dose for monotherapy. In another embodiment, the prescribed dosage of the DA D3/D4 receptor antagonist is at or below the typically described dose for monotherapy, and the $(5\text{-}HT)_{2C}$ receptor agonist is prescribed at a dosage that is above the typically described dose for monotherapy.

It is especially advantageous to formulate compositions of the invention in unit dosage form for ease of administration and uniformity of dosage. The term "unit dosage forms" as used herein refers to physically discrete units suited as unitary dosages for the individuals to be treated. That is, the compositions are formulated into discrete dosage units each containing a predetermined, "unit dosage" of an active compound calculated to produce the desired therapeutic effect in association with the required pharmaceutical carrier. The specifications of the novel dosage unit forms of the invention are dependent on the unique characteristics of the composition containing the DA D3/D4 receptor antagonist and $(5\text{-}HT)_{2C}$ receptor agonist and the particular therapeutic effect to be achieved. Dosages can further be determined by reference to the usual dose and manner of administration of the ingredients. It is also within the scope of the present invention to formulate a single physically discrete dosage form having each of the active ingredients of the combination treatment (e.g., a single dosage form having a DA D3/D4 receptor antagonist and a $(5\text{-}HT)_{2C}$ receptor agonist).

The method of administration of compositions or combinations of compositions will depend, in particular, on the type of DA D3/D4 receptor antagonist and $(5\text{-}HT)_{2C}$ receptor agonist. The DA D3/D4 receptor antagonist and $(5\text{-}HT)_{2C}$ receptor agonist may be administered together in the same composition or simultaneously or sequentially in two separate compositions. Also, one or more DA D3/D4 receptor antagonist and $(5\text{-}HT)_{2C}$ receptor agonist may be administered to a subject or patient either in the form of a therapeutic composition or in combination, e.g., in the form of one or more separate compositions administered simultaneously or sequentially. The schedule of administration will be dependent on the type of DA D3/D4 receptor antagonist and $(5\text{-}HT)_{2C}$ receptor agonist chosen.

DA D3/D4 receptor antagonist and $(5\text{-}HT)_{2C}$ receptor agonist can also be administered along with a pharmaceutically acceptable carrier. As used herein "pharmaceutically acceptable carrier" includes any solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in compositions of the invention is contemplated.

A DA D3/D4 receptor antagonist or a $(5\text{-}HT)_{2C}$ receptor agonist alone, or in combination with a $(5\text{-}HT)_{2C}$ receptor agonist or DA D3/D4 receptor antagonist, is preferably administered orally. When the composition(s) are orally administered, an inert diluent or an assimilable edible carrier may be included. The composition and other ingredients may also be enclosed in a hard or soft shell gelatin capsule, compressed into tablets, or incorporated directly into the individual's diet. For oral therapeutic administration, the composition may be incorporated with excipients and used in the form of ingestible tablets, buccal tablets, troches, capsules, elixirs, suspensions, syrups, wafers, and the like. The percentage of the compositions and preparations may, of course, be varied. The amount of active compound in such therapeutically useful compositions is such that a suitable dosage will be obtained. In a particular embodiment, the present invention includes pharmaceutical composition comprising a therapeutically effective amount of a DA D3/D4 receptor antagonist and a $(5\text{-}HT)_{2C}$ receptor agonist. In one embodiment, the present invention includes a therapeutically-effective amount of a DA D3/D4 receptor antagonist and a $(5\text{-}HT)_{2C}$ receptor agonist packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

The tablets, troches, pills, capsules and the like may also contain a binder, an excipient, a lubricant, or a sweetening agent. Various other materials may be present as coatings or to otherwise modify the physical form of the dosage unit. For instance, tablets, pills, or capsules may be coated with shellac, sugar or both. Of course, any material used in preparing any dosage unit form should be pharmaceutically pure and substantially non-toxic in the amounts employed.

A DA D3/D4 receptor antagonist or a $(5\text{-}HT)_{2C}$ receptor agonist, alone or in combination with DA D3/D4 receptor antagonist or a $(5\text{-}HT)_{2C}$ receptor agonist, can also be administered in a convenient manner such as by injection (subcutaneous, intravenous, etc.), inhalation, transdermal application, or rectal administration. Depending on the route of administration, the composition containing the DA D3/D4 receptor antagonist and/or $(5\text{-}HT)_{2C}$ receptor agonist may be coated with a material to protect the compound from the action of acids and other natural conditions, which may inactivate the compounds or compositions.

To administer the compositions, for example, transdermally or by injection, it may be necessary to coat the composition with, or co-administer the composition with, a material to prevent its inactivation. For example, the composition may be administered to an individual in an appropriate diluent or in an appropriate carrier such as liposomes. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27). To administer the compositions containing one or more of a DA D3/D4 receptor antagonist and/or a $(5\text{-}HT)_{2C}$ receptor agonist parenterally or intraperitoneally, dispersions can be prepared in glycerol, liquid polyethylene glycols, and mixtures thereof and in oils. Under ordinary conditions of storage and use, these preparations may contain a preservative to prevent the growth of microorganisms.

Compositions suitable for injectable use include sterile aqueous solutions (where water soluble) or dispersions and sterile powders for the extemporaneous preparation of sterile injectable solutions or dispersion. In all cases, the composition should be sterile and fluid to the extent that easy syringability exists. Compositions should be stable under the conditions of manufacture and storage, and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Various antibacterial and antifungal agents can achieve prevention of the action of microorganisms. In many cases, it will be preferable to include isotonic agents, for example, sugars, polyalcohols such as mannitol and sorbitol, or sodium chloride in the composition. Prolonged absorption of the injectable compositions can be brought about by including in the composition an agent that delays absorption, for example, aluminum monostearate and gelatin.

One aspect of the present invention features prescribing a DA D3/D4 receptor antagonist and a $(5\text{-}HT)_{2C}$ receptor agonist to treat addiction. A typical dose for each component can be between about 2 to 600 mg daily, including but not limited to doses of 2, 5, 10, 20, 30, 40, 50, 60, 70, 80, 90, 100, 125, 150, 200, 300, 400, 500, to 600 mg daily, including all values and ranges there between.

Yet another embodiment of the present invention features pharmaceutical compositions (e.g., for oral administration) comprising DA D3/D4 receptor antagonist and a $(5\text{-}HT)_{2C}$ receptor agonist in a single pharmaceutical formulation. Such compositions may be preferred, for example, to increase patient compliance (e.g., by reducing the number of administrations necessary to achieve the desired pharmacologic effect).

A. Additivity/Synergy

Compositions of one or more DA D3/D4 receptor antagonist in combination with one or more $(5\text{-}HT)_{2C}$ receptor agonist are synergistically effective. Synergy is defined as the interaction of two or more agents so that their combined effect is greater than the sum of their individual effects. For example, if the effect of drug A alone in treating a disease is 25%, and the effect of drug B alone in treating a disease is 25%, but when the two drugs are combined the effect in treating the disease is >50%, the effect of A and B is synergistic.

Additivity is defined as the interaction of two or more agents so that their combined effect is more than each individually and as much as the sum of their individual effects.

An improvement in the drug therapeutic regimen can be described as the interaction of two or more agents so that their combined effect reduces the incidence of adverse event (AE) of either or both agents used in co-therapy. This reduction in the incidence of AE can be a result of, e.g., administration of lower dosages of either or both agent used in the co-therapy. For example, if the effect of Drug A alone is 25% and has an AE incidence of 45% at labeled dose; and the effect of Drug B alone is 25% and has an AE incidence of 30% at labeled dose, but when the two drugs are combined at lower than labeled doses of each, if the overall effect is 35% and the adverse incidence rate is 20%, there is an improvement in the drug therapeutic regimen.

B. Reduced Side Effects/Other Benefits

Combination therapies can allow DA D3/D4 receptor antagonist and $(5\text{-HT})_{2C}$ receptor agonist to be administered in lower dosages to avoid side effects. In doing so, the dose of each compound, required for mono-therapy, is reduced and the safe therapeutic range is extended.

C. Equivalents

Those skilled in the art will recognize, or be able to ascertain using no more than routine experimentation, numerous equivalents to the specific procedures described herein. Such equivalents are considered to be within the scope of the present invention and are covered by the following claims and the current specification. Various substitutions, alterations, and modifications may be made to the invention without departing from the spirit and scope of the invention as defined by the claims.

II. Addiction

Addiction is a physical or psychological dependence on a substance or an activity that may be harmful to the addict or can interfere with the addict's normal life. Many drugs, both illegal and legal, which may include prescription drugs, can cause a physical or psychological dependence. Illicit drug addiction has a negative impact on society, as addicts tend to resort to crime to support their addiction. Examples of illegal addictive substances include: cocaine, marijuana, opiates, sedatives and amphetamines. Legal substances that can be addictive include caffeine, alcohol, nicotine, and some prescription medications. Activities that can become addictive to the point that they interfere with the addict's normal life include: gambling, shopping, exercise, work, computer usage, internet usage, computer games, sex, cleaning and washing.

Cocaine is a commonly used, addictive, illicit drug, obtained from the leaves of the coca plant. Cocaine addiction is characterized by obsessive, compulsive drug consumption that is difficult to stop. Statistically, cocaine addicts that manage to stop their addiction exhibit a high rate of relapse as craving for cocaine remains after stopping use. In addicted users, abrupt stopping of cocaine usage can bring about withdrawal symptoms, such as paranoia, depression, sleep disturbances and anxiety. Cocaine addiction is commonly treated by psychotherapy in rehabilitation centers, but dropout rates in such programs are high. The withdrawal symptoms and the vulnerability to relapse make it difficult to succeed in providing a long-term cure for cocaine addiction.

In many addicts, cue reactivity is exhibited. Cue reactivity is a phenomenon in which an addict physiologically or psychologically responds to a stimulus related to his addiction. In many situations, exposure to a cue associated with an addict's past use of cocaine will elicit and/or increase craving in an addict. For example, for a person addicted to cigarette smoking or a person in a process of breaking an addiction to cigarette smoking, the smell of cigarette smoke or seeing another person light a cigarette may induce craving for a cigarette. For an alcoholic or alcoholic in rehabilitation, the sound of wine glasses clinking may induce a craving for alcohol. For a cocaine addict, seeing drug related paraphernalia may be a cue that induces craving. Cue reactivity may continue for long after the addictive behavior has stopped, increasing a risk that an addict may return to his or her addiction. Many rehabilitation programs encourage addicts to avoid "addiction" cues to facilitate their rehabilitation process.

In some embodiments, the addiction to be treated or prevented as disclosed herein is a physical dependence to an agent (an addictive agent) or to a particular behavioral pattern. The addiction expressing a physical dependence may be to an agent generally selected from illicit drugs, prescription drugs (and OTC drugs), alcohol or any combination thereof, which agent is referred to herein as the "addictive agent". Generally speaking, the agent causes a recurring compulsion by an individual to engage in use and abuse of the agent, despite harmful consequences to the individual's health, mental state or social life. The term "addictive behavior" similarly refers to a behavioral compulsion, such as gambling, and compulsive overeating, as further detailed herein below.

In some embodiments, the addiction is caused by an addictive agent, being optionally selected amongst addictive recreational drugs and addictive medications.

In some embodiments, the addictive agent is selected from alcohol, caffeine, nicotine, *Cannabis* and *Cannabis* derivatives, opiates and morphine-like compounds, phencyclidine and phencyclidine-like compounds, sedative hypnotics, psycho-stimulants, amphetamines and amphetamine-related drugs.

In additional embodiments, the addictive agent is selected from alcohol, caffeine, nicotine, *Cannabis*, morphine, heroin, codeine, cocaine, hydrocodone, hydromorphone, levorphanol, metapon, nalorphine, naloxone, naltrexone, oxycodone, oxymorphone, tramadol, ethoheptazine, fentanyl, levorphanol, meperidine, methadone, phenazocine, propoxyphene, sufentanil, phencyclidine, benzodiazepines, methaqualone, mecloqualone, etaqualone, pemoline, amphetamine, methamphetamine, methylenedioxymethamphetamine, dextroamphetamine, methylamphetamine, and synthetic derivatives of cathinone.

In other embodiments, the addictive agent is selected amongst pain-killer such as alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene sufentanil, tramadol, tilidine and any combination of any of the aforementioned agents.

In yet additional embodiments, the addictive agent is selected from apomorphine, beta-hydroxy 3-methylfentanyl, carfentanil, dihydroetorphine, dioxaphetylbutyrate, methadyl acetate, papaverine, remifentanil, thebaine, and tramadol.

In some embodiments, the addiction is to cocaine.

In some embodiments, the addiction is in the form of a compulsive behavior (addictive behavior) and may be selected from obsessive compulsive disorder, compulsive spending and/or gambling, pathological overeating, pathological use of electronic devices and communication devices such as cellular phones, pathological use of electronic video games, addiction to pornography and sex, eating disorders such as anorexia and bulimia, kleptomania, pyromania, compulsive over-exercising and overworking.

In some embodiments, the addiction is to two or more addictive agents and/or addictive behavior. In some embodiments, one or both of the addictions are to an addictive agent.

If the treatment according to methods described herein is not successful, treatment can be repeated, for example, by repeating the treatment protocol.

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Therapeutic Potential of DA $D_3$ Receptor Antagonists for Drug Addiction

Given the importance of DA in mediating the abuse-related related effects of cocaine, DA receptor antagonists have received considerable attention as potential medications for cocaine abuse. Both DA $D_1$-like ($D_1$, and $D_5$), and $D_2$-like ($D_2$, $D_3$, and $D_4$) receptor antagonists reduce cocaine self-administration by laboratory animals, suggesting that all 5 DA receptor subtypes might contribute to the abuse-related effects of cocaine. While effective in preclinical studies, the DA $D_1$-like antagonist ecopipam (SCH 39166) has generally failed to alter the subjective or reinforcing effects of cocaine in humans at doses that did not produce sedation. A similar lack of effect has also been reported for DA $D_2$ receptor-preferring antagonists, such as haloperidol; however, it is difficult to determine the degree to which these negative results are impacted by the onset of extrapyramidal side effects, typical of DA $D_2$ receptor antagonists.

Although AEs preclude further development of DA $D_2$ receptor-selective antagonists, the DA $D_3$ receptor has received considerable attention as a target for treating cocaine abuse, based on three key features of the receptor: (1) DA $D_3$ receptors are primarily expressed in limbic regions of the brain, including those central to reward, such as the NAcc meaning that DA $D_3$ receptor antagonists are largely devoid of dose-limiting extrapyramidal effects; (2) the expression of DA $D_3$ receptors is upregulated in rats with a history of repeated cocaine administration as well as in the brains of human cocaine overdose fatalities; and (3) antagonists and partial agonists selective for the DA $D_3$ receptor decrease cocaine self-administration and inhibit the reinstatement of a response previously reinforced by cocaine. While these findings suggest that the DA $D_3$ receptor should be a viable target for medications aimed at treating cocaine abuse, there are currently no FDA-approved DA $D_3$ receptor-selective antagonists to test this hypothesis in humans.

In recent years, buspirone has emerged as a somewhat surprising candidate to test the DA $D_3$ receptor hypothesis of cocaine abuse. Although originally developed as a DA $D_2$-like receptor antagonist, buspirone was found to be more effective at treating anxiety than psychoses, an effect that is thought to be due to its partial agonist effects at 5-HT1A receptors rather than its antagonist actions at DA $D_2$ receptors. Buspirone (at doses up to 60 mg) was approved in 1986 for treating generalized anxiety disorder. Despite this apparent selectivity for 5-HT1A receptors (relative to DA $D_2$ receptors), recent studies suggested that buspirone is roughly equipotent at 5-HT1A, DA $D_3$, and DA $D_4$ receptors. Based on its relatively selective binding profile at DA $D_3$ receptors (~5-70 fold) buspirone was selected as a viable, FDA-approved medication to test the DA $D_3$ receptor hypothesis of cocaine abuse. Although buspirone reliably decreased cocaine self-administration in rhesus and cynomolgus monkeys, it failed to alter the reinforcing effects of cocaine in a human laboratory study (30 mg) and failed to prolong abstinence from cocaine use in a multi-site, randomized, double-blind, placebo-controlled pilot study (60 mg). However, it is important to note that imaging data from Volkow and colleagues suggest that a 3-fold larger dose of buspirone would be required to effectively treat addiction.

Figure 2:
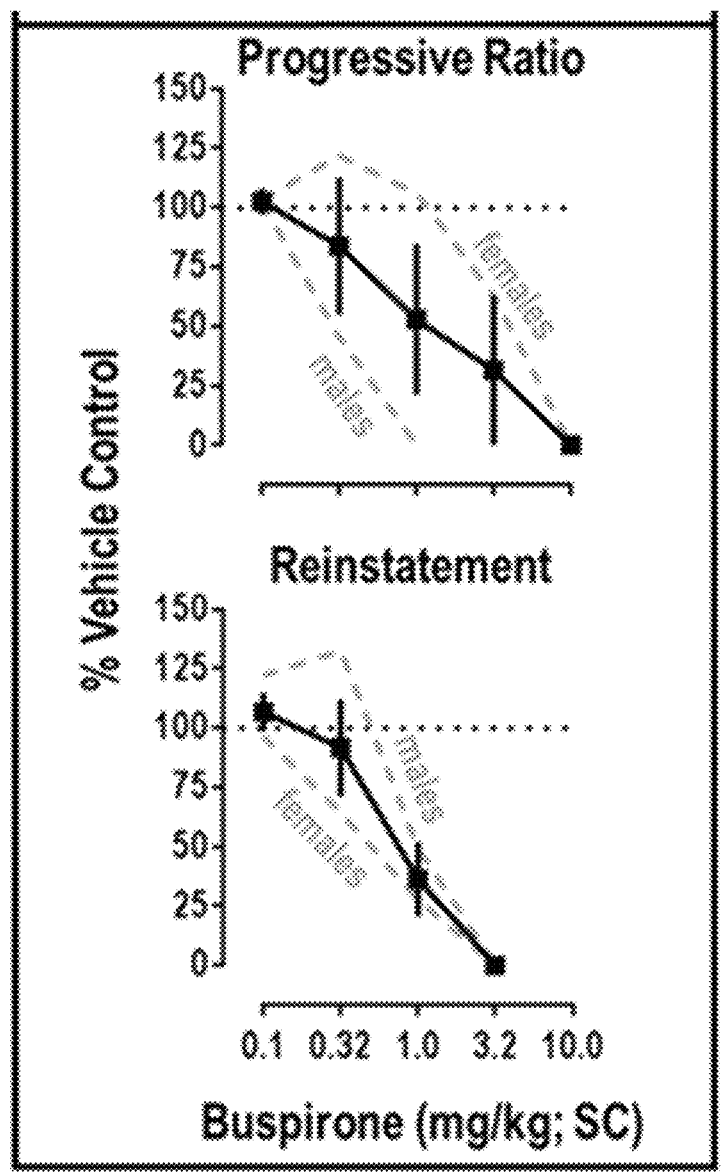
FIG. 2. Effects of buspirone on responding maintained by 0.032 mg/kg/inf cocaine (PR), or reinstated by 0.32 m/kg cocaine in 4 rhesus monkeys, 2 female and 2 male.

Preliminary data from the inventors' laboratory confirm and extend reports by Bergman and colleagues and show that buspirone dose-dependently decreases the reinforcing effectiveness of cocaine when responding is maintained under a progressive ratio (PR) schedule of reinforcement (FIG. 2; top panel), as well as the effectiveness of cocaine to reinstate extinguished responding for cocaine (FIG. 2; bottom panel). Moreover, preliminary data from 4 monkeys (2 male and 2 female), suggest that buspirone is ~10-fold more potent in males than in females at decreasing cocaine self-administration under the PR schedule (FIG. 2). Interestingly, clinical data support this sex-related difference, with the 60 mg dose of buspirone being more effective at promoting abstinence in males than in females.

While preclinical studies strongly suggest that buspirone could be an effective treatment for cocaine abuse, its failure to alter clinical endpoints of cocaine abuse when administered at doses as large as 60 mg suggests that larger doses and/or different formulations (e.g., buspirone:locaserin mixtures) are needed. The inventors contemplated that mixtures of buspirone and lorcaserin may exhibit supra-additive interactions with regard to their effectiveness to reduce the abuse-related effects of cocaine, then clinically relevant outcomes would likely be achieved with drug mixtures comprising a dose of buspirone well below the FDA-approved maximum dose of 60 mg.

Therapeutic Potential of 5-$HT_{2C}$ Receptor Agonists for Drug Addiction

Serotonin (5-HT) systems play an important and well-documented role in modulating goal-directed behaviors, such as feeding. Based in large part on evidence that 5-$HT_{2C}$ receptors mediate the hypophagic effects of direct and indirect-acting 5-HT receptor agonists, significant efforts have been devoted towards developing selective 5-$HT_{2C}$ receptor agonists in the hopes of identifying drugs that decrease appetite without also producing cardiovascular toxicities (5-HT23 receptor-mediated) or hallucination (5-HT2A receptor-mediated) common to less selective and/or indirect-acting 5-HT drugs. Interestingly, and of direct relevance to this application, in addition to reducing food intake, 5-$HT_{2C}$ receptor agonists also decrease cocaine self-administration, consistent with a more general role for 5-$HT_{2C}$ receptors in regulating food- and drug-motivated behaviors.

In the decades since these initial discoveries, substantial progress has been made towards understanding the molecular, neuro- and behavioral pharmacology of 5-$HT_{2C}$ receptors. Although mounting evidence suggests that anti-obesity effects are mediated by 5-$HT_{2C}$ receptors on pro-opiomelanocortin neurons located in brain regions important for feeding (e.g., dorsomedial and paraventricular nucleus of the hypothalamus), the anti-addiction effects of 5-$HT_{2C}$ receptor agonists are thought to be mediated by their capacity to modulate mesolimbic DA neurotransmission. Indeed, 5-$HT_{2C}$ receptors are highly expressed on both the soma and dendrites of DA and GABA neurons within the ventral tegmental area (VTA) as well as on DA nerve terminals within the NAcc, a pattern of distribution that allows 5-$HT_{2C}$ receptors to play an important role in controlling the activity of DA systems under both basal and activated conditions, including modulation of cocaine-induced increases in DA within the NAcc.

Consistent with their capacity to inhibit DAergic responses to cocaine, a variety of agonists with preferential activity at 5-$HT_{2C}$ receptors (e.g., Ro 60-0175, MK 212, mCPP, WAY-163909, and CP-809,101) have been shown to decrease cocaine self-administration and/or inhibit the reinstatement of a response previously reinforced by cocaine. Although these findings provide strong support for the hypothesis that activation of 5-$HT_{2C}$ receptors decreases the abuse-related effects of drugs, it is unclear whether 5-$HT_{2C}$ agonists have similar effects in humans.

Lorcaserin is a 5-$HT_{2C}$ receptor agonist reported to be ~20-fold selective for 5-$HT_{2C}$ over 5-HT2A receptors and ~100-fold selective for 5-$HT_{2C}$ over 5-$HT_{2B}$ receptors, based on functional assays in cells transfected with human 5-$HT_{2A, 2B,}$ or $_{2C}$ receptors. After a series of multicenter, placebo-controlled trials showing that lorcaserin produced modest, but sustained weight loss, coupled with improvements in weight-related health measures (e.g., blood pressure, cholesterol, diabetes), in 2012 the FDA approved lorcaserin (maximum dose of 10 mg, twice daily) for use in obese adults with at least one weight-related health condition. Interestingly, when administered to recreational drug users, supra-therapeutic doses of lorcaserin (20-60 mg) produced subjective ratings of "high", "good drug effects" and "hallucination", effects consistent with agonist actions at 5-$HT_{2A}$ receptors, and significant enough to prompt the DEA to designate lorcaserin as Schedule IV. It was recently reported that lorcaserin produces 5-$HT_{2A}$ receptor-mediated head-twitches, a rodent model of hallucination, at doses comparable to those required to reduce body weight in rats.

Consistent with the premise that 5-$HT_{2C}$ receptor agonists decrease the abuse-related effects of drugs, the inventors recently reported that acute administration of lorcaserin dose-dependently inhibits cocaine self-administration under both fixed ratio and PR schedules of reinforcement in rhesus monkeys. In addition, these studies also showed that the anti-cocaine effects of lorcaserin were (1) apparent at doses of lorcaserin that also produced other 5-$HT_{2C}$ receptor-mediated behavioral effects, (2) not due to a pharmacokinetic interaction between cocaine and lorcaserin, and (3) persisted for at least 14 days of repeated (daily) treatment with lorcaserin. Similar acute effects of lorcaserin have also been reported in rats self-administering cocaine, nicotine, or ethanol.

Figure 3:
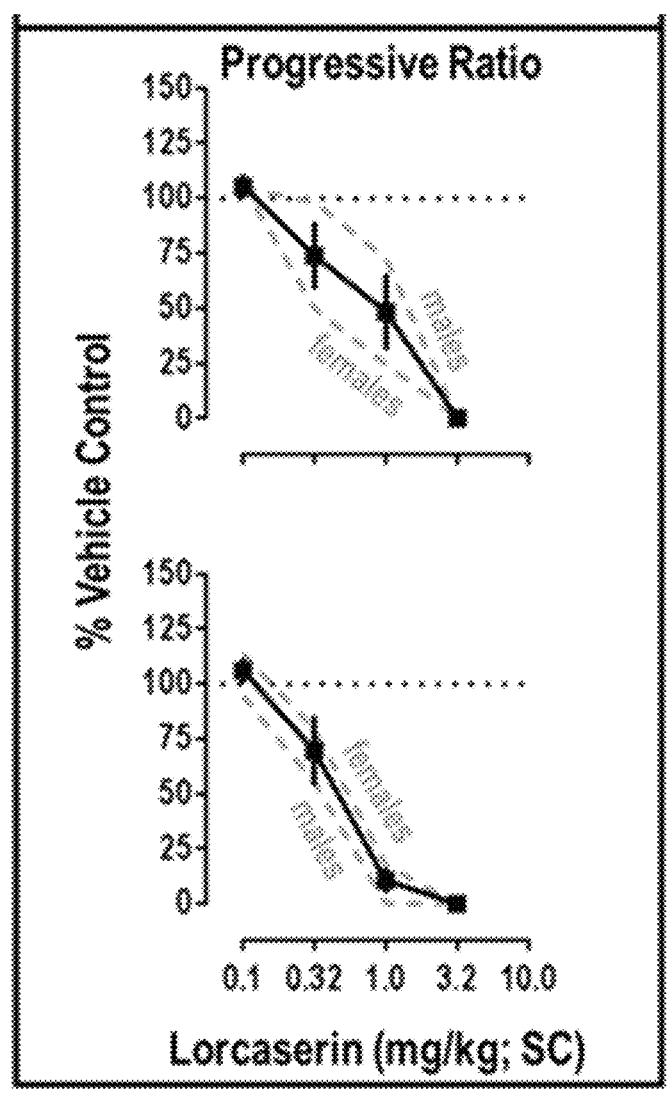
FIG. 3. Effects of lorcaserin on responding maintained by 0.032 mg/kg/inf cocaine (PR), or reinstated by 0.32 m/kg cocaine in 4 rhesus monkeys, 2 males and 2 females.

Preliminary data collected in the same 4 monkeys that were used to evaluate buspirone (FIG. 2) confirm our original findings and demonstrate that lorcaserin dose-dependently decreases the reinforcing effectiveness of cocaine when responding is maintained under a PR schedule of reinforcement (FIG. 3; top panel), as well as the effectiveness of cocaine to reinstate an extinguished response for cocaine (FIG. 3; bottom panel). Although smaller in magnitude than observed for buspirone, sex-related differences in the potency of lorcaserin to decrease cocaine self-administration were also observed; however, unlike for buspirone, females were slightly (~3-fold) more sensitive than males to lorcaserin.

Consistent preclinical evidence demonstrating that 5-$HT_{2C}$ receptor agonists reduce abuse-related effects of cocaine has spurred clinical efforts to rapidly and rationally repurpose lorcaserin for the treatment of cocaine use disorder. Although there are no published data on the effectiveness of lorcaserin to reduce cocaine effects in humans, there are currently 4 safety and effectiveness trials registered with ClinicalTriails.gov. A Phase I trial has been completed but not reported (NCT02393599), and two other Phase I trials are currently recruiting subjects (NCT02537873 and NCT02680288). A multi-site Phase II trial of lorcaserin for the treatment of cocaine use disorder has also been registered, but has not yet begun recruiting subjects. However, it is important to remember that doses of lorcaserin only slightly larger than those approved/required to produce its therapeutic effects have been reported to produce feelings of "high" and "hallucinations" in humans, and to induce head-twitching in rodents, all of which are consistent with agonist actions at 5-HT2A receptors. Thus, there is a clear need to develop formulations/treatment strategies that minimize the total dose of lorcaserin required to effectively reduce cocaine use and/or prolonging abstinence from cocaine use. Studies will thoroughly evaluate the hypothesis that drug mixtures containing lorcaserin and buspirone are more potent and/or effective at decreasing cocaine self-administration and/or inhibiting the reinstatement of extinguished responding for cocaine, than would be predicted based on the effects of either drug alone (i.e., smaller doses of each drug would be required to produce the same therapeutic effect).

The inventors have begun to use nonhuman primates to evaluate FDA-approved medications for treating cocaine abuse. While the rational repurposing of FDA-approved drugs has the potential to dramatically reduce the time and cost associated with getting effective treatments for cocaine (and other drug) abuse into the clinic, translating positive preclinical effects to clinically relevant outcomes has been challenging. In a recent review describing progress (and setbacks) in the preclinical development and clinical evaluation of medications for cocaine abuse, Czoty and colleagues used the d-amphetamine prodrug lisdexamfetamine as a case study to highlight some of the major hurdles in translating preclinical success to effective therapies in the clinic. As they describe, even when drugs such as lisdexamfetamine consistently reduce cocaine self-administration in nonhuman primates, they are often ineffective at improving cocaine abstinence when evaluated in a clinical setting. Although differences in the endpoints (i.e., reductions in preclinical drug-taking versus complete abstinence in the clinic) likely impact measures of clinical efficacy, Mooney and colleagues point out that their evaluation of lisdexamfetamine was limited to the doses that are approved to treat attention-deficit hyperactivity disorder (ADHD) and that larger doses likely would have resulted in a positive clinical outcome. A similar conclusion was reached after buspirone consistently decreased cocaine taking in preclinical studies, but failed to prolong complete abstinence from cocaine in a clinical setting. In fact, Volkow and colleagues concluded that in order to achieve a clinically relevant level of DA $D_3$ receptor occupancy, buspirone would have to be administered at doses at least 3-fold larger than the 60 mg maximal dose approved for treating anxiety. Thus, in addition to developing novel therapeutics, there is a clear need to develop strategies to enhance/augment the potency and/or effectiveness of FDA-approved drugs so that abstinence from cocaine use can be achieved with doses that are already approved to treat other conditions.

Figure 4:
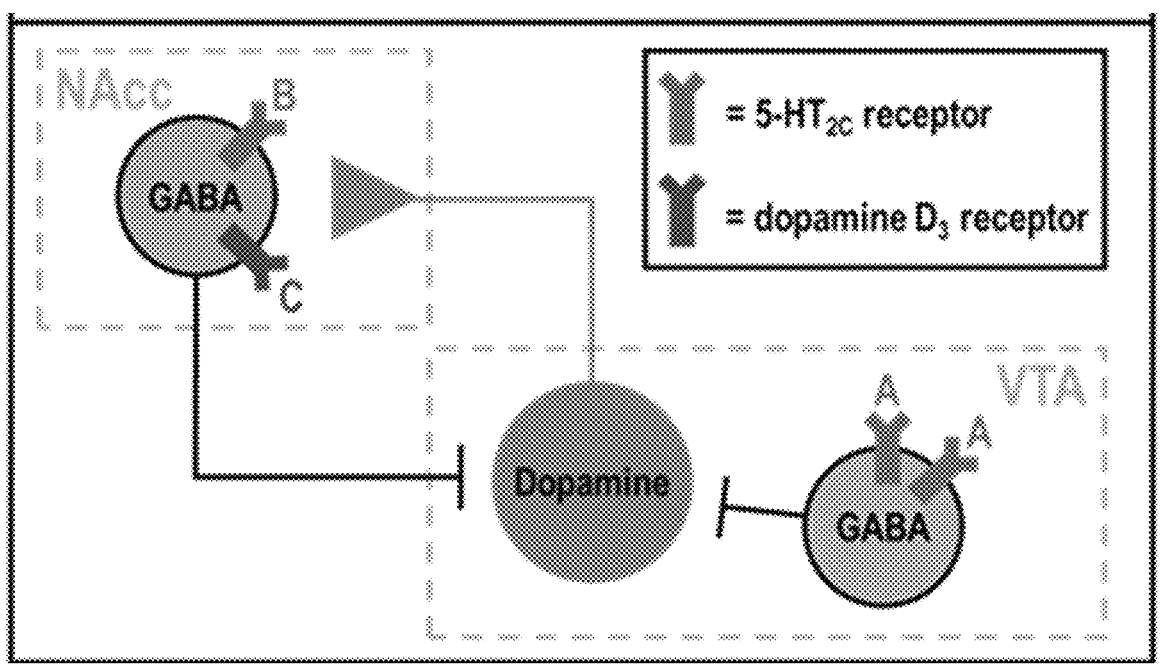
FIG. 4. Simplified schematic of the mesolimbic DA system showing the proposed sites of interaction between lorcaserin and buspirone. Activation of 5-HT$_{2C}$ receptors localized on GABAergic neurons within the VTA (labeled as A in the figure) of NAcc (labeled as B in the figure) would enhance GABAergic inhibition of DAergic neurons projecting form the VTA to the NAcc. Likewise, antagonism of post-synaptic DA D3 receptors (labeled as C in the figure) within the NAcc would enhance GABAergic inhibition of mesolimbic DAergic neurotransmission.

Studies described herein evaluate mixtures of drugs that target both pre- (e.g., 5-HT$_{2C}$ receptors) and post- (e.g., DA D3 receptors) synaptic regulators of DA neurotransmission produce a therapeutic effect (e.g., decrease in drug taking, reinstatement, etc.) that is greater than the effect of either drug alone (i.e., supra-additive interaction). Based in large part on their capacity to modulate the activity of mesolimbic DA neurons (FIG. 4 and described above), the inventors have chosen to evaluate lorcaserin, an FDA-approved drug with 5-HT$_{2C}$ receptor agonist properties, and buspirone, an FDA-approved drug with DA D$_3$ receptor antagonist properties. Through its actions on 5-HT$_{2C}$ receptors located on GABAergic neurons in the VTA and NAcc (FIG. 4), lorcaserin inhibits the activity of mesolimbic DA neurons projecting from the VTA to the NAcc, thereby decreasing the effectiveness of cocaine to increase synaptic DA levels. Similarly, by antagonism at DA D$_3$ receptors within the NAcc (FIG. 4) and other structures, buspirone not only prevents the propagation of cocaine-induced increases in DA signaling, but also enhances the GABAergic inhibition of mesolimbic DA neurons. Because both of the drugs that will be used to evaluate this hypothesis are approved by the FDA, the results of the proposed studies will not only be novel, but also highly translatable to the clinic.

In addition, proposed studies will combine state-of-the-art self-administration (PR and food-cocaine choice), reinstatement procedures, and radio-telemetric assessments of cardiovascular effects with sophisticated dose-addition analyses (FIG. 5) to quantify and characterize the nature of the interaction(s) between lorcaserin and buspirone for both therapeutic and potentially AEs. Data obtained in 4 rhesus monkeys show that when mixed at fixed-dose ratios of their ED$_{50}$ (i.e., dose required to decreased PR responding for 0.032 mg/kg/inf cocaine by 50%), lorcaserin and buspirone are more potent and effective at decreasing cocaine self-administration than would be predicted for an additive interaction. For example, dose-response curves for the 1:1 and 1:3 mixtures of lorcaserin and buspirone were shifted ~3 to 5-fold to the left of the predicted additive dose-response curve, indicating a supra-additive interaction. Not only do these results provide strong support, but they also suggest that it should be possible to reduce the dose of both drugs while maintaining, and possibly enhancing, the therapeutic effectiveness of lorcaserin and buspirone.

Figure 5:
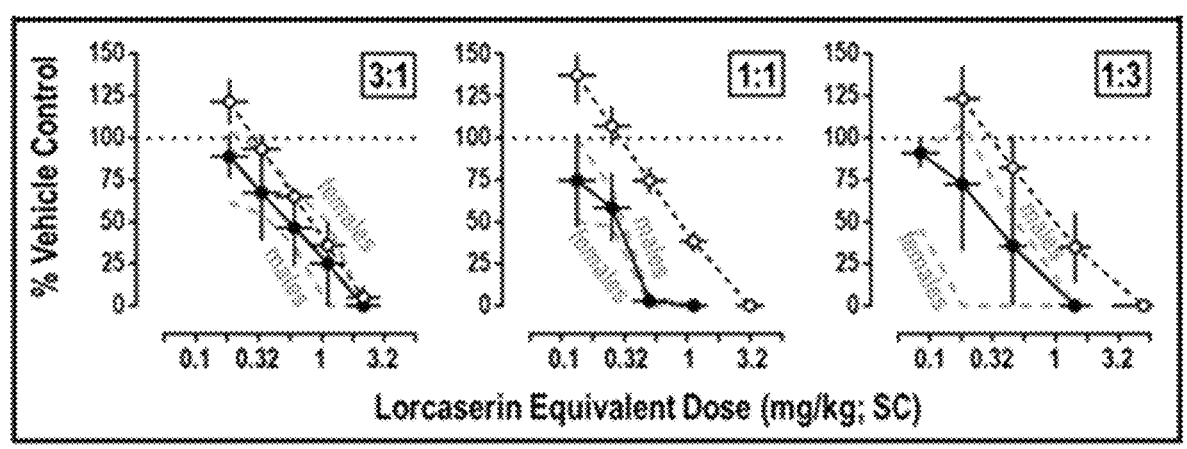
FIG. 5. Effectiveness of mixtures of lorcaserin and buspirone, administered at 3:1, 1:1, and 1:3 fixed-dose ratios of lorcaserin:buspirone (relative to the ED$_{50}$ of each drug) to reduce PR responding for cocaine (0.032 mg/kg/inf cocaine). Dose addition analyses were used to determine the predicted additive effect level for each dose combination (total dose expressed as lorcaserin equivalents). Experimentally determined effects are expressed as the group mean for 4 rhesus monkeys as well as the mean of 2 males and 2 females.

Interestingly, and consistent with the large sex-related differences observed for the effects of buspirone alone (FIG. 2), sex-related differences were also observed for some of the drug mixtures, with females being ~10-fold more sensitive than males to the 1:3 lorcaserin:buspirone mixture (FIG. 5). While this effect was somewhat surprising given that females were less sensitive to the effects of buspirone alone (an effect that is consistent with clinical reports that buspirone is less effective at promoting abstinence in females than in males), these findings suggest that combinations of lorcaserin and buspirone might be particularly effective at reducing cocaine use in females. However, because of the small sample size (2 males and 2 females) it is premature to conclude that these differences are necessarily related to sex rather than some other underlying individual difference that happened to co-vary with sex.

Experimental Subjects. A total of 20 adult rhesus monkeys (10 male and 10 female) will be used in confirmation studies. Power analyses were conducted using historical and preliminary data for each assay (PR, choice, reinstatement, and cardiovascular). Based on these results, power analyses (Student t-test for independent samples; PASS 2011, Kaysville, Utah) show an "n" of 10 (5 males and 5 females) to be sufficient to detect, with 80% power, a shift of at least 2-fold in the dose-response curves for self-administration and reinstatement (effects of lorcaserin and buspirone alone, as well as departures from additivity), and a 20% difference in cardiovascular endpoints. These calculations assume that underlying sex-related differences exist for each endpoint, and result in studies that are adequately powered to detect significant effects using both within and between sex analyses.

Inhibition of Drug-Taking and Drug-Seeking. Development of pharmacotherapies for cocaine abuse is complicated by the fact that they should effectively block not only the direct reinforcing effects of the cocaine, but also drug-seeking behaviors thought to be important indicators of relapse. Studies used a simple (i.e., single alternative; respond or not) PR schedule of self-administration as well as a reinstatement procedure to demonstrate that lorcaserin and buspirone are both effective at decreasing the reinforcing effectiveness (PR) and relapse-related effects (reinstatement) of cocaine (FIG. 2 and FIG. 3). That lorcaserin and buspirone both produce the same effect (decrease in responding) means that they are well suited for using dose-addition analyses to characterize the nature of drug-drug interactions; however, this approach alone might not capture the complexity of human drug-taking behavior. Thus, in conjunction with PR and reinstatement procedures, mixtures of lorcaserin and buspirone will also be evaluated in rhesus monkeys responding under food-cocaine choice procedure. The inclusion of food-cocaine choice is advantageous for several reasons, but mostly because the particular variant of the choice procedure and has become one of the more widely used assays to evaluate candidate medications for drug abuse, thus facilitating direct comparisons not only across assays (PR and choice) but also across laboratories.

A. General Procedures

Surgical preparation. All monkeys will be surgically prepared with an indwelling venous catheter connected to a subcutaneous vascular access port located in the mid-scapular region as we have previously described.

Apparatus. Self-administration studies will be conducted in custom-built, ventilated, and sound attenuating operant chambers. Monkeys seated in primate chairs will face an instrument panel with two response levers and a centrally located food pellet receptacle. Stimulus lights located above each lever can be illuminated green or red to signal cocaine availability or the delivery of a cocaine infusion, respectively. Infusions are delivered via a syringe driver connected to the vascular access port by an IV extension set and a 20-g Huber-point needle. Experimental events are controlled and recorded by a PC running Med-PC IV software (Med-Associates, St. Albans, Vt.).

Progressive ratio (PR). Studies will specifically evaluate using the hypothesis that drug mixtures containing lorcaserin and buspirone are more potent and/or effective at reducing responding for cocaine under a PR schedule (i.e., a direct measure of reinforcing effectiveness). The inventors have extensive experience with this schedule that generates monotonic dose-response curves that are relatively straightforward to interpret and ideally suited for quantitative analyses, such as the dose-addition analyses that will be used to characterize the nature of the interaction(s) between lorcaserin and buspirone.

Experimental design. Monkeys (5 males and 5 females) can respond for saline or cocaine (0.0032-0.32 mg/kg/inf) under the same PR schedule of reinforcement are used to evaluate lorcaserin and buspirone administered alone and as binary mixtures (FIG. 2, FIG. 3, and FIG. 5). Briefly, sessions will last a maximum of 4 hrs, but terminate if an infusion is not delivered within 40 min (i.e., 40-min limited hold). Completion of the initial response requirement (50 responses) will result in an infusion paired with a 5-sec presentation of the drug-associated stimuli (light above active lever will switch from green to red), and the initiation of a 180-sec timeout period during which all stimulus lights will be extinguished with responses recorded but having no scheduled consequence. For subsequent infusions, the response requirement will increment according to the following equation: ratio=[5e^(infusion number*0.2)]-5, which corresponds to the following ratio values (50, 62, 77, 95, 118, 145, 178, 219, 268, 328, 402, 492, 603, 737 . . . ). Designation of the active lever will be counterbalanced across monkeys.

Similar to methods used to obtain the preliminary PR data (FIG. 2 and FIG. 3), studies will first evaluate the acute effects of lorcaserin (0.1-3.2 mg/kg; SC; 15-min PT) and buspirone (0.1-3.2 mg/kg; SC; 15-min PT) alone prior to evaluating the effects of mixtures. Because the nature of drug-drug interactions (e.g., additive, sub-additive, supra-additive) can vary depending upon the ratio at which they are mixed, the inventors will evaluate at least three fixed-ratios (i.e., 3:1, 1:1, and 1:3, lorcaserin:buspirone) relative to the dose of each drug required to produce a 2-fold shift in the cocaine dose-response curve (Table 1). In order to accurately estimate the dose pair of each fixed-ratio mixture required to shift the cocaine dose-response curve 2-fold to the right, at least three fixed-dose pairs are evaluated for each fixed-ratio mixture (Table 1), with smaller or larger dose pairs evaluated as needed (Table 1). Although evaluation of the 3:1, 1:1, and 1:3 fixed-ratio mixtures of lorcaserin:buspirone allows for conditions in which each constituent drug contributes 25%, 50%, or 75% of the total drug effect, this range will be extended to 10:1 or 1:10 if significant, non-additive interactions are observed with either the 3:1 or 1:3 fixed-ratio mixtures, respectively. Although the inventors have previously used grouped data to determine the composition of drug mixtures, because preliminary studies identified apparent sex-related differences in the effects of buspirone (FIG. 2), data (FIG. 5) used mixtures that were customized for individual monkeys. Because it is expected to observe individual (sex-related) differences in the effects of buspirone and/or lorcaserin alone, proposed studies will customize drug mixtures for each monkey, hypothetical examples of which are shown below for a 1:1 mixture of lorcaserin and buspirone (Table 1). Each fixed-dose pair will be evaluated from a stable baseline (i.e., 2 consecutive vehicle-treated sessions in which the number of infusions varies by <2) and followed by at least 2 vehicle-treated sessions to ensure that responding returns to pre-treatment levels. Acute effects of dose pairs will be evaluated with each dose of cocaine prior to chronic dosing studies.

TABLE 1

| | hypothetical $ED_{2\text{-}fold}$[A] | | 1:1 lorcaserin:buspirone (mg/kg) | | | | |
|---|---|---|---|---|---|---|---|
| | | | dose pair 1 | dose pair 2 | dose pair 3 | dose pair 4 | dose pair 5 |
| | lorcaesrin | buspirone | LOR:BUS[C] | LOR:BUS[B] | LOR:BUS[B] | LOR:BUS[B] | LOR:BUS[C] |
| male | 1.0 mg/kg | 0.56 mg/kg | 0.16:0.09 | 0.28:0.16 | 0.50:0.28 | 0.89:0.50 | 1.58:0.89 |
| female | 0.56 mg/kg | 3.2 mg/kg | 0.09:0.51 | 0.16:0.90 | 0.28:1.6 | 0.50:2.85 | 0.89:5.06 |

[A] dose required to produce a 2-fold rightward shift in the cocaine dose-response curve;
[B] fixed-dose pairs of lorcaserin and buspirone for a 1:1 ratio of their $ED_{2\text{-}fold}$s;
[C] dose pairs that will only be evaluated if needed to determine the $ED_{2\text{-}fold}$ for a particular fixed-ratio mixture of lorcaserin and buspirone (i.e., 3:1, 1:1, or 1:3).

It has been shown that lorcaserin and buspirone retain their effectiveness to reduce cocaine self-administration when administered daily for 10-14 days; however, it is unclear whether the apparent supra-additive interactions observed between lorcaserin and buspirone (FIG. 5) persist across repeated daily dosing. Thus, in addition to evaluating the acute effects of lorcaserin:buspirone mixtures, proposed studies will also evaluate the effectiveness of at least two fixed-dose pairs of each fixed-ratio (e.g., dose pairs 3 and 4 of the 3:1, 1:1, and 1:3 mixtures) to modify the cocaine dose-response curve when administered once daily for 14 days.

Figure 6:
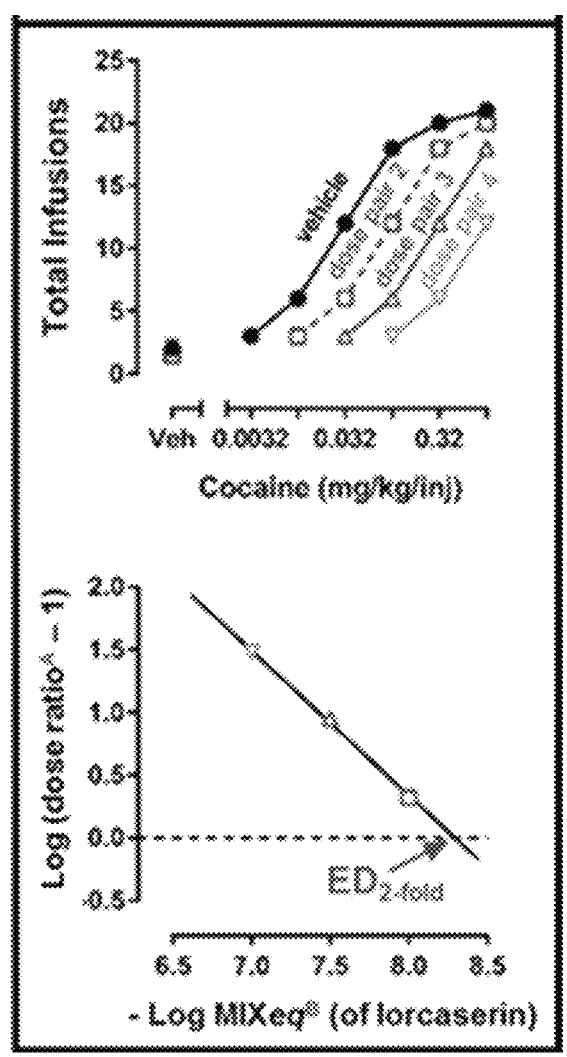
FIG. 6. Hypothetical data showing rightward shifts in the cocaine dose-response curve, and estimation of $ED_{2\text{-}fold}$ value for a specific fixed-ratio mixture of lorcaserin and buspirone.

Dependent variables of interest. The primary dependent variable will be the reinforcing effectiveness of each unit dose of cocaine (i.e., the average number of infusions earned during the 2 sessions that satisfy stability criteria) under both vehicle and mixture treated conditions. These data will be used to construct dose-response curves for cocaine self-administration (FIG. 6; top panel), which will be analyzed by linear regression to obtain an $ED_{50}$ value for cocaine under each condition. Dose ratios ($ED_{50}$ dose pair/$ED_{50}$ vehicle; FIG. 6) will be used to determine the magnitude of the shift produced by each fixed-dose pair (expressed as total equivalent dose of lorcaserin; MIXeq; FIG. 6). Using concepts (but not underlying assumptions) similar to those Schild applied to estimate the apparent affinity of antagonists, the Log (dose ratio −1) and −Log MIXeq are used to obtain an estimate of the total equivalent dose of lorcaserin (MIXeq) required to produce a 2-fold shift in the cocaine dose-response curve for each fixed-ratio mixture of lorcaseirn and buspirone (FIG. 6) under both acute and repeated dosing conditions.

Dose-addition analyses provide a powerful approach to characterize the nature of the interaction between two drugs that produce the same pharmacologic effect. Using properties derived from the dose-response curves for each drug alone (i.e., potency, effectiveness, and slope), the concept of dose equivalence can be applied to convert the unit dose of one drug (e.g., buspirone) to an equivalent dose of the other drug (e.g., lorcaserin) after which the doses can be summed to determine the total dose in terms of lorcaserin equivalents (mg/kg) for each fixed-dose pair. This can then be used to calculate the predicted additive effect for each fixed-dose pair, as was done for preliminary studies using a single dose of cocaine (FIG. 5). By extrapolating this method to other doses of cocaine, it is possible to construct a predicted additive dose-response curve for each dose pair of each fixed-ratio mixture which can then be subjected to the same analyses as the experimentally observed data described above, ultimately resulting in a predicted additive $ED_{2\text{-}fold}$ value for each fixed-ratio mixture of lorcaserin and buspirone in each monkey. Potency ratios (observed $ED_{2\text{-}fold}$/predicted $ED_{2\text{-}fold}$) will be calculated for each monkey at each fixed-ratio, with ratios smaller than 1 (i.e., 95% CI does not include 1) indicating that a particular fixed-ratio mixture of lorcaserin and buspirone was significantly more potent than predicted for an additive interaction (i.e., supra-additive), whereas ratios not different from or larger than 1 would indicate an additive or sub-additive interaction, respectively.

Expected results, interpretations & alternative approaches. With regard to the effects of constituent drugs alone, it is expected that both lorcaserin and buspirone produce dose-dependent rightward shifts in the cocaine dose-response curve, consistent with preliminary data (FIG. 2 and FIG. 3) and previously published reports on lorcaserin.

Acute administration. Based on preliminary data obtained in 4 monkeys (2 males and 2 females; FIG. 5) the inventors predict that fixed-ratio mixtures of lorcaserin and buspirone will be more potent than predicted at decreasing the reinforcing effectiveness of cocaine, based on the effects of each drug alone (i.e., mixture $ED_{2\text{-}fold}$ smaller than predicted $ED_{2\text{-}fold}$). In addition, the inventors expect that the magnitude (nature) of these interactions will likely vary as a function of the mixture ratio, with the 3:1 mixture of lorcaserin and buspirone exhibiting strictly additive effects and the 1:1 and 1:3 mixtures exhibiting supra-additive effects (i.e., shifted to the left of the predicted additive dose-response; FIG. 5). It is unclear whether supra-additive interactions will occur with larger fixed-ratios (e.g., 1:10) and the interaction might to return to additivity as the ratio increases (e.g., 1:10, 1:30 . . . ).

Repeated administration. Cocaine abuse is a chronic disease, and effective treatment will undoubtedly require daily administration over a period of weeks or months. It has been previously shown that tolerance does not develop to the effects of lorcaserin or buspirone following repeated, daily administration (10-14 days). Based on these findings, the inventors expect that the nature of the acute interaction for mixtures of lorcaserin and buspirone (e.g., additive, sub-additive, or supra-additive) will persist across a 14-day treatment period.

Sex-related differences. Preliminary data (FIG. 2. and FIG. 3) suggest that lorcaserin alone will be slightly more potent in female than in male monkeys, whereas buspirone alone will be significantly less potent in female than in male monkeys; the latter is consistent with sex-related differences in the effects of buspirone reported for human cocaine users. In addition, preliminary data (FIG. 5; right panel) suggest that the 1:3 mixture of lorcaserin and buspirone will be more potent/effective in females than in males, as evidenced by smaller $ED_{2\text{-}fold}$ values (and observed $ED_{2\text{-}fold}$/predicted $ED_{2\text{-}fold}$ ratios). Such an outcome would indicate that the magnitude of the supra-additive interaction between lorcaserin and buspirone is greater in females than in males. Although the magnitude of these effects is expected to vary as a function of sex, the inventors expect that the nature of the interaction (i.e., additive, supra-additive, sub-additive) will be the same in males and females. In addition, any sex-related differences observed following acute administration are expected to persist throughout the 14-day repeated administration study (i.e., sex-related differences are not expected in the development of tolerance or sensitization).

Potential problems & alternative approaches. The inventors have extensive experience with dose-addition analyses and this PR procedure (FIG. 3 and FIG. 5) and do not expect any technical problems. Although the inventors have previously shown that lorcaserin produces rightward shifts in the cocaine dose-response curve under this PR schedule, data from Bergman and colleagues suggest that the effects of buspirone might not be surmounted (i.e., downward rather than rightward shifts). If such an effect is observed, the inventors will modify the data analyses to more closely match what was used to determine the nature of the interaction(s) between lorcaserin and buspirone for the preliminary data (FIG. 4) in which a single dose of cocaine was available (i.e., inhibition curves rather than $ED_{2\text{-}fold}$ analyses).

Cocaine-food choice behavior. Studies will evaluate and confirm the hypothesis that lorcaserin:buspirone mixtures are more potent and/or effective at shifting responding away from cocaine and towards food following both acute and repeated administration. The food-drug choice paradigm was chosen because it is uniquely suited to model aspects of drug abuse that are important for treatment but not well captured by other assays, and because it typically generates monotonic dose-response curves that are amenable to the dose-addition analyses that will be used to characterize the nature of the interaction(s) between lorcaserin and buspirone.

Experimental design. The inventors have extensive experience using choice procedures to investigate the determinants of drug reinforcement in monkeys. For proposed studies, the parameters of the choice procedure were chosen to closely match those originally described by Negus, and subsequently used to evaluate a large number of candidate medications for cocaine abuse, including buspirone and lorcaserin. Adoption of these parameters will allow for the effects of mixtures of lorcaserin and buspirone to be compared directly to other candidate medications. Briefly, monkeys (5 males and 5 females) will respond under a 5 component, concurrent schedule in which food pellets are delivered according to an FR100:TO30-sec schedule on one lever and cocaine infusions are delivered according to an FR30:TO30-sec schedule on the alternate lever. During the first component, monkeys choose between a food pellet and no cocaine (i.e., only cocaine-paired stimuli), with choice between food and increasingly larger unit doses of cocaine (0.0032, 0.01, 0.032, and 0.1 mg/kg/inf) evaluated across components #2-5. Each component comprises 10 choice trials and lasts a total of 20 min; a 5-min blackout separates components. A solid white stimulus light above the food lever will signal food availability and a green stimulus light above the cocaine lever will signal cocaine availability. Under no cocaine conditions (component #1), this light will be constantly illuminated; however, during components #2-5 it will flash at increasingly faster rates (e.g., 1, 2, 3 and 4 Hz) to signal increasingly larger unit doses of cocaine. Under these conditions, responding will be considered stable when the first component in which 80% choice of cocaine is observed varies by <0.5 log units for 2 consecutive sessions.

Studies will evaluate the effects of lorcaserin (0.1-3.2 mg/kg; SC; 15-mm PT) and buspirone (0.1-3.2 mg/kg; SC; 15-min PT) alone prior to evaluating the effects of mixtures. Because this range of cocaine doses generally results in monotonically increasing dose-response curve for percentage cocaine choice. Briefly, at least three fixed-dose pairs (i.e., dose pairs 2, 3, and 4; Table 1) of at least three fixed-ratio mixtures of lorcaserin and buspirone (i.e., 3:1, 1:1, and 1:3 relative the $ED_{2\text{-}fold}$ for each drug to shift the cocaine choice dose-response curve) will be evaluated in random order, with all dose pairs for a given mixture evaluated before studying the next fixed-ratio mixture. The acute effects of drug mixtures will be evaluated first, with repeated dosing experiments performed only after a sufficient number of dose pairs have been evaluated to determine an $ED_{2\text{-}fold}$ for each of the fixed-ratio mixtures. The range of fixed-dose ratios will be extended (e.g., to 10:1 or 1:10) as needed and repeated dosing of each dose pair will be evaluated over 14 consecutive days.

Dependent variables of interest. The primary dependent variables will be the number of trials completed and the percentage cocaine choice, across the 5 components. Because choice procedures also allow for the detection of gross behavioral disruptions (increased latency to respond and/or decreased rate), only data from components in which 4 or more choice trials are completed (i.e., 40%) will be analyzed. These data will be used to construct dose-response curves for percentage cocaine choice, which will be analyzed by linear regression to obtain $ED_{50}$ values for cocaine under vehicle, and treatment conditions (i.e., each set of fixed-dose pairs for each fixed-ratio mixture). Likewise, $ED_{2\text{-}fold}$ values for each dose pair will be used to estimate the $ED_{2\text{-}fold}$ value for each fixed-ratio mixture. Estimated $ED_{2\text{-}fold}$ values for each fixed-ratio mixture will be compared to the predicted $ED_{2\text{-}fold}$ value to obtain potency ratios (observed $ED_{2\text{-}fold}$/predicted $ED_{2\text{-}fold}$) for each monkey at each fixed-ratio under acute and repeated dosing conditions. Potency ratios smaller than 1 will be interpreted as supra-additive, whereas ratios not different from or larger than 1 will be interpreted as additive or sub-additive, respectively.

Reinstatement of responding for cocaine. Studies will use the same 10 monkeys used for cocaine-primed/cue-induced reinstatement procedure to evaluate the hypothesis that acute and repeated administration of mixtures of lorcaserin and buspirone result in a supra-additive inhibition of relapse-related behaviors. This procedure was chosen because the inventors have previously shown it to be sensitive to the effects of both lorcaserin and buspirone and because it is possible to obtain within subject inhibition curves that are well-suited to the dose-addition analyses that will be used to characterize the nature of the interaction(s) between lorcaserin and buspirone.

Experimental design. Monkeys will respond for 0.032 mg/kg/inf cocaine under a FR30:TO180-sec schedule of reinforcement during daily 90-min sessions. During extinction, all stimulus lights will be extinguished with responding being recorded but having no scheduled consequence. During reinstatement tests, the drug-associated stimuli (i.e., the green and red stimulus lights) will be presented according to an FR30:TO180-sec schedule but no infusions will be delivered. Priming infusions of cocaine or saline will be injected directly into the vascular access port (followed by a 5-ml saline flush) 5 min before the start of the session. The inventors have extensive experience with this procedure, having used it to characterize the effects of lorcaserin alone on cocaine-primed and cue-induced reinstatement in rhesus monkeys.

The acute effects of lorcaserin (0.1-3.2 mg/kg; SC; 15 min PT) and buspirone (0.1-3.2 mg/kg; SC; 15 min PT) alone will be studied prior to evaluating mixtures. Because the nature of drug-drug interactions can vary depending upon the composition of the mixture, lorcaserin and buspirone will be evaluated over at least three fixed-dose pairs of at least three fixed-ratios (i.e., 3:1, 1:1, and 1:3), using the strategy described above. Mixtures will be based on the effects of lorcaserin and buspirone alone and customized to individual monkeys. Reinstatement tests will be separated by at least 5 sessions (3 cocaine self-administration sessions and 2 extinction sessions). Additional fixed-ratios mixtures (10:1 or 1:10) will be evaluated if significant, non-additive interactions are observed with either 3:1 or 1:3 ratios, respectively.

Similar to the methods used to characterize the effectiveness of lorcaserin to reduce cocaine-primed reinstatement following repeated administrations, the effectiveness of mixtures to inhibit the reinstatement response will also be evaluated after daily administrations. Briefly, these procedures will be identical to those described above (0.032 mg/kg/inf cocaine self-administration→extinction→reinstatement) with the exception that pretreatments (i.e., mixtures or vehicle) will be administered 15-min before the start of 13 consecutive daily extinction sessions (i.e., saline prime, no stimuli), with the effectiveness of the pretreatment to reduce cocaine-primed reinstatement evaluated during the 14th session (i.e., 0.32 mg/kg cocaine prime, cocaine-associated stimuli).

Dependent variables of interest. The primary dependent variables of interest will be the number of active and inactive lever responses made during each of three types of sessions: (1) cocaine self-administration; (2) extinction; and (3) reinstatement. The effects of lorcaserin, buspirone and their binary mixtures will be normalized to the reinstatement response observed under control conditions (i.e., vehicle pretreatment followed by a 0.32 mg/kg cocaine prime). These data will be used to construct inhibition curves for the effects of lorcaserin, buspirone, and their binary mixtures, with dose-addition analyses similar to those used in preliminary studies used to determine if the effects of mixtures differ from the predicted additive inhibition curve. Experimentally determined and predicted additive inhibition curves will be analyzed by linear regression to obtain $ED_{50}$ values (i.e., dose required to reduce the reinstatement response by 50%) which will then be used to obtain potency ratios (observed $ED_{50}$/predicted $ED_{50}$) for each monkey at each fixed-ratio. Potency ratios less than 1 (i.e., 95% CI does not include 1) will be interpreted as supra-additive, whereas potency ratios greater than or not different from 1 will be interpreted as sub-additive or additive, respectively.

Expected results, interpretations & alternative approaches. Consistent with published data from the inventors' laboratory, the inventors expect lorcaserin and buspirone to dose-dependently inhibit the reinstatement of responding for cocaine, a preclinical model of relapse-related behaviors. These predictions are also supported by a growing body of evidence indicating that agonists targeting 5-$HT_{2C}$ receptors and antagonists targeting DA D3 receptors prevent drug-primed reinstatement in both rodents and non-human primates.

Acute administration. Consistent with the effects of lorcaserin and buspirone alone, acute administration of fixed-ratio mixtures of lorcaserin and buspirone are expected to dose-dependently inhibit the reinstatement of responding by cocaine primes and cocaine-associated stimuli. Based on the inventors hypothesis regarding synergistic interactions between drugs that target pre-synaptic (lorcaserin) and post-synaptic (buspirone) regulators of DA neurotransmission, the inventors expect that mixtures of lorcaserin and buspirone will be more potent/effective (for at least some fixed-ratios) at preventing the reinstatement response than would be predicted for a strictly additive interaction. Additive interactions are also likely to occur, although the inventors do not expect to observe sub-additive interactions for any of the fixed-ratio mixtures.

Repeated administration. Because drug abuse is a chronic disease characterized by high rates of relapse, pharmacotherapies aimed at prolonging abstinence will need to be administered repeatedly (or in long-acting formulations). Consistent with previous studies showing that lorcaserin and buspirone both retain their effectiveness to reduce abuse-related effects of cocaine across repeated administrations, the inventors expect that mixtures will prevent reinstatement across a 14-day repeated dosing period. That is to say, if a particular mixture is found to be supra-additive during acute tests, the inventors expect it will continue to be supra-additive when evaluated over 14 days of repeated administration. Although it is difficult to predict whether the nature/magnitude of the interaction/effect will translate across endpoints, preliminary data obtained under the PR schedule suggest that supra-additivity is possible between lorcaserin and buspirone. A similar supra-additive interaction in the reinstatement studies would provide strong evidence that a combination therapy comprising lorcaserin and buspirone would be an effective pharmacotherapy for cocaine abuse, despite significant reductions in the total dose of both drugs.

Sex-related differences. Preliminary data suggest that, unlike with cocaine self-administration, the potency and/or effectiveness of lorcaserin or buspirone to inhibit the reinstatement response will not differ as a function of sex. Despite expectations that sex will not impact the effects of the constituent drugs alone, it is possible that sex-related differences will emerge when lorcaserin and buspirone are administered as a mixture.

Cardiovascular Effects. Lorcaserin and buspirone are devoid of serious cardiovascular complications (e.g., valvulopathies common to 5-HT2B receptor agonists) and appear to be safe when administered in combination with cocaine (NIDA has advanced lorcaserin from Phase I safety [NCT02393599] to Phase 11 efficacy [NCT03007394] trials). However, it is unclear whether cardiovascular complications will emerge when lorcaserin and buspirone are administered as mixtures, and/or when mixtures of lorcaserin and buspirone are administered in conjunction with cocaine.

Characterize the cardiovascular effects of lorcaserin:buspirone mixtures administered alone and with cocaine in male and female rhesus monkeys. Studies under this aim will test the hypothesis that the cardiovascular (mean arterial pressure [MAP], heart rate [HR], and ECG parameters) and locomotor effects of lorcaserin and buspirone are not altered when administered as a mixture, and that mixtures do not exacerbate, and may blunt, the cardiovascular effects of cocaine; these effects are not expected to differ as a function on sex.

Experimental design. Rhesus monkeys (5 males and 5 females from Aim 1b) previously instrumented with IV catheters will be surgically prepared with a radio-telemetric probe (DSI model L11) capable of collecting real-time measures of systemic blood pressure, ECG, and heart rate as the inventors have described previously. Monkeys will be fitted with a jacket and tether system that allows free movement within the homecage and remote administration of IV infusions. Because lorcaserin and buspirone are safe when administered to humans either alone (i.e., FDA-approved) or in combination with cocaine, these studies are primarily designed to assess potential cardiovascular interactions between (1) lorcaserin and buspirone (in mixtures) and (2) lorcaserin and buspirone mixtures and cocaine.

Briefly, cardiovascular recordings will occur in the homecage, with at least 15 min of baseline recordings collected prior to SC administration of saline or a mixture of lorcaserin and buspirone. An IV infusion of either saline or cocaine (0.32 and 1 mg/kg) will be administered 15 min later, and recordings will be collected for at least 2 hrs. The inventors have previously used implantable telemetry to characterize the cardiovascular effects of a full range of doses (i.e., ineffective to toxic). Because bolus IV infusions of 0.1 mg/kg cocaine are ineffective, and because bolus IV infusions of 3.2 mg/kg cocaine are only slightly lower than those that produce severe AEs, these studies will investigate interactions between lorcaserin:buspirone mixtures and doses of cocaine that reliably increase cardiovascular activity, without also increasing risk for AEs of cocaine (e.g., convulsion, myocardial infarct, death). Because these studies are aimed at evaluating the cardiovascular effects of mixtures that might be used to treat cocaine abuse, the composition of each fixed-dose mixture will be based on the mean potency of lorcaserin and buspirone to reduce the cocaine-maintained and cocaine-induced behaviors. However, because the effects of buspirone and/or lorcaserin are expected to vary as a function of sex, the composition of the mixtures tested will vary as a function of sex. Females will be tested with mixtures based on mean $ED_{2\text{-}fold}$ values obtained in females, whereas males will be tested with mixtures based on mean $ED_{2\text{-}fold}$ values obtained in males. Each mixture will be evaluated at three fixed-dose pairs (e.g., dose pairs 2, 3, and 4; Table 1) of three fixed-ratio (3:1, 1:1, and 1:3) mixtures, with each condition evaluated as a pretreatment to saline and 1.0 mg/kg cocaine. Tests will be conducted once per week, with cocaine tested on alternating weeks in order to avoid the potential development of sensitization to the cardiovascular effects of cocaine.

The cardiovascular effects of lorcaserin:buspirone mixtures will be evaluated following both acute and repeated treatments. For repeated administration studies, the cardiovascular effects of fixed dose pairs of lorcaserin:buspirone mixtures will be assessed over 14 consecutive days of treatment, with mixture-cocaine interactions evaluated on treatment day 7 (0.32 mg/kg cocaine) and on treatment day 14 (1 mg/kg cocaine).

Dependent variables of interest. As in previous studies, telemetric probes will be used in conjunction with activity monitoring collars to collect real-time measures of locomotor activity, body temperature, MAP, HR, and ECG parameters (e.g., QRS interval [QRSi], corrected QT interval [QT cf], and ST elevation [STe]). These values will be collected once every second and analyzed across 5-min blocks according to methods we have previously used to characterize the cardiovascular effects of 0.32 and 1.0 mg/kg cocaine in rhesus monkeys.

Because lorcaserin:buspirone mixtures will be based on potencies to affect cocaine-maintained behaviors, and because lorcaserin and buspirone are unlikely to have the same profile of cardiovascular effects, dose-addition analyses are not well suited to analyze these data. Instead, drug mixtures will be evaluated for their capacity to significantly alter the locomotor activity, body temperature, or cardiovascular parameters when administered as pretreatments to either saline or cocaine. Time course of acute effects (i.e., across the 120-min observation period) will be analyzed by two-factor (mixture dose, time) repeated measures ANOVAs, with the time course of mixture-cocaine interactions evaluated by three-factor (mixture, cocaine dose, and time) repeated measure ANOVAs. For repeated dosing experiments, the area under the time course curve for each endpoint will be compared across time (day 1, 2, 3 . . . ) using one-factor (day) repeated measure ANOVAs. Similarly, mixture-cocaine interactions following acute and repeated mixture administration will be compared using one-factor (test) repeated measure ANOVAs.

The invention claimed is:

1. A method of treating an addictive behavior in a subject, the method comprising administering to the subject an effective amount of a serotonin (5-HT)$_{2c}$ receptor agonist, wherein the 5-HT$_{2c}$ receptor agonist is lorcaserin, CP 809101, Ro-60-0175, WAY 161503, WAY 163909, MK 212, meta-chlorophenylpiperazine (mCPP), 1-methylpsilocin, Org 12962 hydrochloride, or salts thereof, in combination with a dopamine (DA) D3/D4 receptor antagonist, wherein the DA D3/D4 receptor antagonist is selected from buspirone, PG 01037, SB 277011A, trifluoperazine, A-381393, L-745,870, L-750,667, L-741,742, S18126, fananserin, clozapine, FAUC 213, sonepiprazole, PD 168568 dihydrochloride, PNU 96415E or salts thereof, or a composition comprising same.

2. The method according to claim 1, wherein the DA D3/D4 receptor antagonist is buspirone.

3. The method according to claim 1, wherein the 5-HT$_{2C}$ receptor agonist is lorcaserin.

4. The method according to claim 1, wherein the addiction is a physical dependence to an addictive agent or to an addictive behavior.

5. The method according to claim 4, wherein the addictive agent is an addictive recreational drug or addictive medication.

6. The method according to claim 4, wherein the addictive agent is Cannabis and Cannabis derivatives, opiates and morphine-like compounds, phencyclidine and phencyclidine-like compounds, sedative hypnotics, psychostimulants, or amphetamines and amphetamine-related drugs.

7. The method according to claim 4, wherein the addictive agent is alcohol, caffeine, nicotine, Cannabis, morphine, heroin, codeine, cocaine, hydrocodone, hydromorphone, levorphanol, metapon, nalorphine, naloxone, naltrexone, oxycodone, oxymorphone, tramadol, ethoheptazine, fentanyl, levorphanol, meperidine, methadone, phenazocine, propoxyphene, sufentanil, phencyclidine, benzodiazepines, methaqualone, mecloqualone, etaqualone, pemoline, amphetamine, methamphetamine, methylenedioxymethamphetamine, dextroamphetamine, or methylamphetamine.

8. The method according to claim 4, wherein the addictive agent is cocaine.

9. The method according to claim 4, wherein the addictive agent is a painkiller or a combination of painkillers.

10. The method according to claim 9, wherein the painkiller is alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene sufentanil, tramadol, or tilidine.

11. The method according to claim 4, wherein the addictive behavior is obsessive compulsive disorder, compulsive spending and/or gambling, pathological overeating, pathological use of electronic devices and communication devices such as cellular phones, pathological use of electronic video games, addiction to pornography and sex, eating disorders such as anorexia and bulimia, kleptomania, pyromania, compulsive over-exercising, or overworking.

12. The method according to claim 1, wherein the addiction is to more than one of an addictive agent and/or addictive behavior.

13. A method for preventing relapse of a subject, the method comprising administering to the subject an effective amount of a 5-HT$_{2c}$ receptor agonist, wherein the 5-HT$_{2c}$ receptor agonist is lorcaserin, CP 809101, Ro-60-0175, WAY 161503, WAY 163909, MK 212, meta-chlorophenylpiperazine (mCPP), 1-methylpsilocin, Org 12962 hydrochloride, or salts thereof, in combination with a dopamine (DA) D3/D4 receptor antagonist, wherein the DA D3/D4 receptor antagonist is selected from buspirone, PG 01037, SB 277011A, trifluoperazine, A-381393, L-745,870, L-750, 667, L-741,742, S18126, fananserin, clozapine, FAUC 213, sonepiprazole, PD 168568 dihydrochloride, PNU 96415E or salts thereof, or a composition comprising same.

14. A method of treating or suppressing relapse to addiction, relapse use of an addictive agent or practice of an addictive or compulsive behavior in a subject, the method comprising administering to the subject in need thereof an effective amount of a 5-HT$_{2c}$ receptor agonist, wherein the 5-HT$_{2c}$ receptor agonist is lorcaserin, CP 809101, Ro-60-0175, WAY 161503, WAY 163909, MK 212, meta-chlorophenylpiperazine (mCPP), 1-methylpsilocin, Org 12962 hydrochloride, or salts thereof, in combination with a dopamine (DA) D3/D4 receptor antagonist, wherein the DA D3/D4 receptor antagonist is selected from buspirone, PG 01037, SB 277011A, trifluoperazine, A-381393, L-745,870, L-750,667, L-741,742, S18126, fananserin, clozapine, FAUC 213, sonepiprazole, PD 168568 dihydrochloride, PNU 96415E or salts thereof, or a composition comprising same.

* * * * *